United States Patent
Dodd et al.

(10) Patent No.: US 10,524,920 B2
(45) Date of Patent: Jan. 7, 2020

(54) PROSTHESIS WITH FIXED OR MOBILE BEARING

(71) Applicants: Biomet UK Limited, Bridgend (GB);
Christopher Dodd, Oxford (GB);
David Wycliffe Murray, Oxford (GB);
John Joseph O'Connor, Oxford (GB)

(72) Inventors: Christopher Dodd, Oxford (GB);
David Wycliffe Murray, Oxford (GB);
John O'Connor, Oxfordshire (GB);
Russell Lloyd, Swindon (GB)

(73) Assignee: Biomet UK Limited, Bridgent South Glamorgan (GB)

( * ) Notice: Subject to any disclaimer, the term of this patent is extended or adjusted under 35 U.S.C. 154(b) by 0 days.

(21) Appl. No.: 15/126,039

(22) PCT Filed: Mar. 27, 2015

(86) PCT No.: PCT/GB2015/050931
§ 371 (c)(1),
(2) Date: Sep. 14, 2016

(87) PCT Pub. No.: WO2015/155505
PCT Pub. Date: Oct. 15, 2015

(65) Prior Publication Data
US 2017/0196696 A1 Jul. 13, 2017

(30) Foreign Application Priority Data
Apr. 11, 2014 (GB) .................. 1406565.0

(51) Int. Cl.
*A61F 2/38* (2006.01)
*A61F 2/30* (2006.01)

(52) U.S. Cl.
CPC ............ *A61F 2/3868* (2013.01); *A61F 2/389* (2013.01); *A61F 2002/3082* (2013.01);
(Continued)

(58) Field of Classification Search
CPC .......... A61F 2/38; A61F 2/3868; A61F 2/389; A61F 2002/3881; A61F 2002/3895
See application file for complete search history.

(56) References Cited

U.S. PATENT DOCUMENTS

| 7,959,680 B2 * | 6/2011 | Stone .................... A61F 2/4081 623/19.11 |
| 2003/0195634 A1 | 10/2003 | Fenning et al. |

(Continued)

FOREIGN PATENT DOCUMENTS

| CN | 101351172 | 1/2009 |
| CN | 103027767 | 4/2013 |

(Continued)

OTHER PUBLICATIONS

Bellier et al. FR 2926719 B1, Mar. 26, 2010, Machine Translation of Foreign document provided in Applicant's IDS.*
(Continued)

*Primary Examiner* — Marcia L Watkins
(74) *Attorney, Agent, or Firm* — Schwegman Lundberg & Woessner, P.A.

(57) ABSTRACT

A prosthesis (100, 200) comprising a bone attachment component (106) having one or more fixation structures (124, 224), wherein the prosthesis is configured to be selectively convertible between a mobile bearing prosthesis, in which a barrier (120) is secured to the bone attachment component (106) using the fixation structures, and a constrained bearing prosthesis, in which a bearing component (204) is secured to the bone attachment component (106) using the fixation structures (124, 224).

7 Claims, 12 Drawing Sheets

(52) U.S. Cl.
CPC ............... *A61F 2002/30504* (2013.01); *A61F 2002/30528* (2013.01); *A61F 2002/30607* (2013.01); *A61F 2002/3895* (2013.01)

(56) References Cited

U.S. PATENT DOCUMENTS

| | | |
|---|---|---|
| 2007/0100463 A1 | 5/2007 | Aram et al. |
| 2010/0222890 A1 | 9/2010 | Barnett et al. |
| 2013/0006375 A1* | 1/2013 | Metzger ............... A61F 2/3868 623/20.31 |
| 2013/0325137 A1 | 12/2013 | Trimmer |
| 2014/0277535 A1 | 9/2014 | Metzger et al. |

FOREIGN PATENT DOCUMENTS

| | | |
|---|---|---|
| CN | 106659570 A | 5/2017 |
| EP | 0529408 A1 | 3/1993 |
| EP | 3128955 A1 | 2/2017 |
| FR | 2926719 A1 | 7/2009 |
| FR | 2926719 | 3/2010 |
| GB | 2525044 A | 10/2015 |
| WO | WO-0226169 A2 | 4/2002 |
| WO | WO-2013046170 A1 | 4/2013 |
| WO | WO-2015155505 A1 | 10/2015 |

OTHER PUBLICATIONS

"European Application Serial No. 15713805.8, Response filed Jun. 19, 2017 to Office Action dated Dec. 16, 2016", 12 pgs.

"Great Britain Application Serial No. 1406565.0, Office Action dated Oct. 29, 2014", 3 pgs.

"International Application Serial No. PCT/GB2015/050931, International Preliminary Report on Patentability dated Oct. 20, 2016", 11 pgs.

"International Application Serial No. PCT/GB2015/050931, International Search Report dated Jun. 18, 2015", 6 pgs.

"International Application Serial No. PCT/GB2015/050931, Written Opinion dated Jun. 18, 2015", 9 pgs.

"Chinese Application Serial No. 201580024925.2, Office Action dated Nov. 16, 2017", (English Translation), 8 pgs.

"Chinese Application Serial No. 201580024925.2, Response filed Mar. 30, 2018 to Office Action dated Nov. 16, 2017", (W/ English Translation of Claims), 12 pgs.

"Chinese Application Serial No. 201580024925.2, Office Action dated Sep. 5, 2018", (W/ English Translation), 14 pgs.

"Chinese Application Serial No. 201580024925.2, Response filed Nov. 20, 2018 to Office Action dated Sep. 5, 2018", (W/ English Claims), 10 pgs.

\* cited by examiner

PROSTHESIS WITH FIXED OR MOBILE BEARING

CLAIM OF PRIORITY

This application is a U.S. National Stage Filing under 35 U.S.C. 371 from International Application No. PCT/GB2015/050931, filed on 27 Mar. 2015, and published as WO 2015/155505 A1 on 15 Oct. 2015, which claims the benefit to United Kingdom Application No. 1406565.0, filed on 11 Apr. 2014 the benefit of priority of each of which is claimed hereby, and each of which are incorporated by reference herein in its entirety.

This invention relates to meniscal prostheses, and particularly, but not exclusively, relates to a knee prosthesis which is selectively convertible between a mobile bearing knee prosthesis and a fixed bearing knee prosthesis.

BACKGROUND

Damage to the articular surfaces or to the ligaments of the knee changes the patterns of movement of the bones on each other and the response of the joint to load. Osteoarthritis follows from failure of the cartilage in one or other of the three joints, leading to bone-on-bone contact and the onset of pain. Frequently, osteoarthritis first manifests itself in the medial compartment, while the ligaments remain intact. The disease can remain confined to the medial compartment until the anterior cruciate ligament fails and the disease then spreads to the other two compartments. No drug treatment has been found which reverses these processes.

Total knee replacement is the most common surgical treatment for osteoarthritis, involving replacement of the articular surfaces of all three compartments and sacrifice of some of the ligaments. Partial knee replacement, for example a unicompartmental knee artheroplasty, involves replacement of the articular surfaces in only one compartment, leaving intact the surfaces of the other two compartments and all of the ligaments. Partial knee replacement can act prophylactically, reducing the rate of development of the disease in the other compartments. Partial knee replacement is surgically more demanding and is not always used when it is indicated.

Mobile bearing arthroplasty may involve fixing metal components to the tibia and the femur. A plastic bearing, an analogue of the natural meniscus, may be positioned between, but not attached to, the metal components fixed to the bones. The metal components are fixed to the bones so as to leave a constant gap between them when the knee is flexed and extended. The surgeon then selects the most appropriate thickness of bearing to fill the gap. The bearing is stuffed between the metal components against the resistance of stretching ligaments. The bearing snaps into position once a thick section of the bearing has passed through the thinnest section of the gap between the fixed components.

A complication that may be associated with mobile bearing arthroplasty is dislocation of the bearing. Dislocation rarely occurs after medial partial knee replacement but is the main complication of lateral arthroplasty. Complete dislocation can occur along the antero-posterior axis of the knee replacement. This can happen either in the anterior direction, as the reverse of the process of implantation, or in the posterior direction. If the patient distracts the joint, i.e. by applying appropriate varus or valgus load to the limb, the bearing may be free to move through an enlarged minimum gap between the femoral and tibial components, which may then come into contact.

Dislocation of a mobile bearing from the lateral side, i.e. towards the inside of the knee, occurs rarely, but could cause damage to the soft tissue. Consequently, it is desirable to mitigate the risk of dislocation of the mobile bearing arthroplasty from the lateral side of the knee prosthesis.

In some circumstances, following dislocation, for example as a result of further degeneration of the knee joint, it becomes necessary to replace the mobile bearing arthroplasty. At revision of these cases, the metal tibial and/or femoral components are usually found to be firmly fixed to the bones, so it is common for the surgeon to replace the worn or damaged mobile bearing arthroplasty with a new bearing of increased thickness, thereby retensioning the joint with a thicker bearing to account for any wear of the prosthesis and/or stretching of the ligaments that may have occurred. However, in cases of severe degeneration it may be necessary to replace the mobile bearing arthroplasty with a fixed bearing arthroplasty. Such a procedure may involve the replacement of the metal component fixed to the tibia, which is an involved and invasive procedure.

Success of the operation, especially that of mobile bearing arthroplasty, depends critically on the presence of intact ligaments. However, the condition of the ligaments cannot be determined with absolute certainty prior to surgery and the decision to use a mobile or fixed bearing can only be made when the joint has been exposed surgically. A typical surgeon is usually an exponent of either fixed or mobile bearing arthroplasty so that, if on exposure, the joint is found to be unsuitable for mobile bearing arthroplasty, the only alternative immedialely available to the surgeon is to perform a much more invasive total knee replacement (TKR). It is desirable to be able to use the same bone preparation techniques to implant both a fixed and mobile bearing prostheses. Equally, when the bones have been cut to accommodate a mobile bearing prosthesis, and the tibial and femoral components have been fitted, it can prove difficult to stabilize the joint with a mobile bearing. It would be useful, therefore, to be able to fix the bearing to the tibial component at that stage.

The present invention seeks to address these issues.

STATEMENTS OF INVENTION

According to the present invention, there is provided a prosthesis comprising: a bone attachment component comprising one or more fixation structures, wherein the prosthesis is configured to be selectively convertible between a mobile bearing prosthesis, in which a barrier, for example a wall, is secured to the bone attachment component using the fixation structures, and a constrained bearing prosthesis, in which a bearing component is secured to the bone attachment component in place of the barrier using the same fixation structures.

The fixation structures may comprise openings or projections. For example, in one embodiment the fixation structures may comprise bores formed at least partially through the bone attachment component, which are adapted to receive cooperating barbed pins which may be fixed to, or pass through the bearing component or the barrier.

According to another aspect of the present invention there is provided a prosthesis comprising: a bone attachment component for supporting a bearing component; and a barrier removably securable to the bone attachment component and configured to limit a range of movement of the bearing component.

The prosthesis may be configured to be selectively convertible between a mobile bearing prosthesis, in which the barrier is secured to the bone attachment component, and a constrained bearing prosthesis, in which the bearing component is secured to the bone attachment component instead of the barrier. The bone attachment component may comprise one or more fixation structures.

According to another aspect of the present invention there is provided a kit of parts for a prosthesis, the kit comprising: at least one bearing component; at least one bone attachment component comprising one or more fixation structures, the bone attachment component being configured to support the bearing component; and at least one barrier which is removably securable to the fixation structures on the bone attachment component, the barrier being configured to limit a range of movement of the bearing component; wherein the prosthesis is selectively convertible between a mobile bearing prosthesis, in which the barrier is secured to bone attachment component using the fixation structures, and a constrained bearing prosthesis, in which the bearing component is secured to the bone attachment component instead of the barrier using the fixation structures.

It is appreciated that the invention may not be limited to the features as described in the above-mentioned aspects and that the present invention may also be provided with one or more of the following optional features.

The barrier may comprise one or more further fixation structures configured to cooperate with the fixation structures on the bone attachment component. The fixation structures may comprise projections and/or openings. For example, the projections may comprise pins and/or pegs. The openings may comprise a recess and/or a hole, e.g. a through-hole or a blind-hole. The fixation structures may comprise one or more retaining members, e.g. clips, barbs and/or hooks. The fixation structures may comprise snap-fit and/or push-fit fixings. The projections may comprise one or more further openings. The further openings may be configured to cooperate with a retaining element, e.g. a pin or similar. The projections may extend through the openings and into a portion of bone. The bone may comprise one or more recesses behind the openings in the bone attachment component. The bone attachment component may be a tibial tray.

The barrier may be configured to cover the fixation structures on the bone attachment component. The barrier may be removably securable to a wall of the bone attachment component. The barrier may be configured to extend the wall of the bone attachment component. The barrier may be removably securable to a bearing surface of the bone attachment component. The barrier may be configured to prevent partial medial dislocation. The barrier may be disposed laterally and/or medially of the bearing component.

The barrier may contact the bearing component at extremes of a range of movement of the bearing component. The barrier may be configured to guard against the dislocation of the bearing component. The barrier may be an anti-dislocation wall. The barrier may comprise a bearing support surface. The barrier may be configured to prevent the bearing component from contacting the bone attachment component. The barrier may be configured to prevent the bearing component from contacting a bone, for example the tibia bone. The barrier may comprise one or more protrusions configured to engage the bearing component at extremes of a range of movement of the bearing component.

The barrier may comprise a tibial wall. The barrier may be configured to cover substantially the whole of an adjacent end of the bone attachment component. The barrier may be at least partially disposed between the bone attachment component and the bearing component. The barrier may be configured to engage one or more grooves on the bone contacting component. The barrier may be removably securable to a wall of the bone attachment component. The barrier may be removably securable to a bearing support surface of the bone attachment component.

The prosthesis may further comprise one or more securing elements configured to connect the bearing component and/or the barrier to the bone attachment component. The securing elements may comprise further fixation structures configured to cooperate with the fixation structures of the barrier, the bone attachment component and/or the fixation structures of the bearing component. The securing elements may be configured to limit the range of movement of the bearing component, for example the securing elements may be configured to substantially limit the range of movement of the bearing component relative to the bone attachment component.

The kit may comprise a securing element configured to connect the bearing component to the bone attachment component. The kit may comprise one or more introducers configured to position the bearing component relative to one or more bone attachment components. The kit may comprise one or more tool, for example a hammer, for use during implantation and/or removal of the prosthesis.

BRIEF DESCRIPTION OF THE DRAWINGS

For a better understanding of the present disclosure, and to show more clearly how it may be carried into effect, reference will now be made, by way of example, to the accompanying drawings, in which.

DETAILED DESCRIPTION

Figure 1:
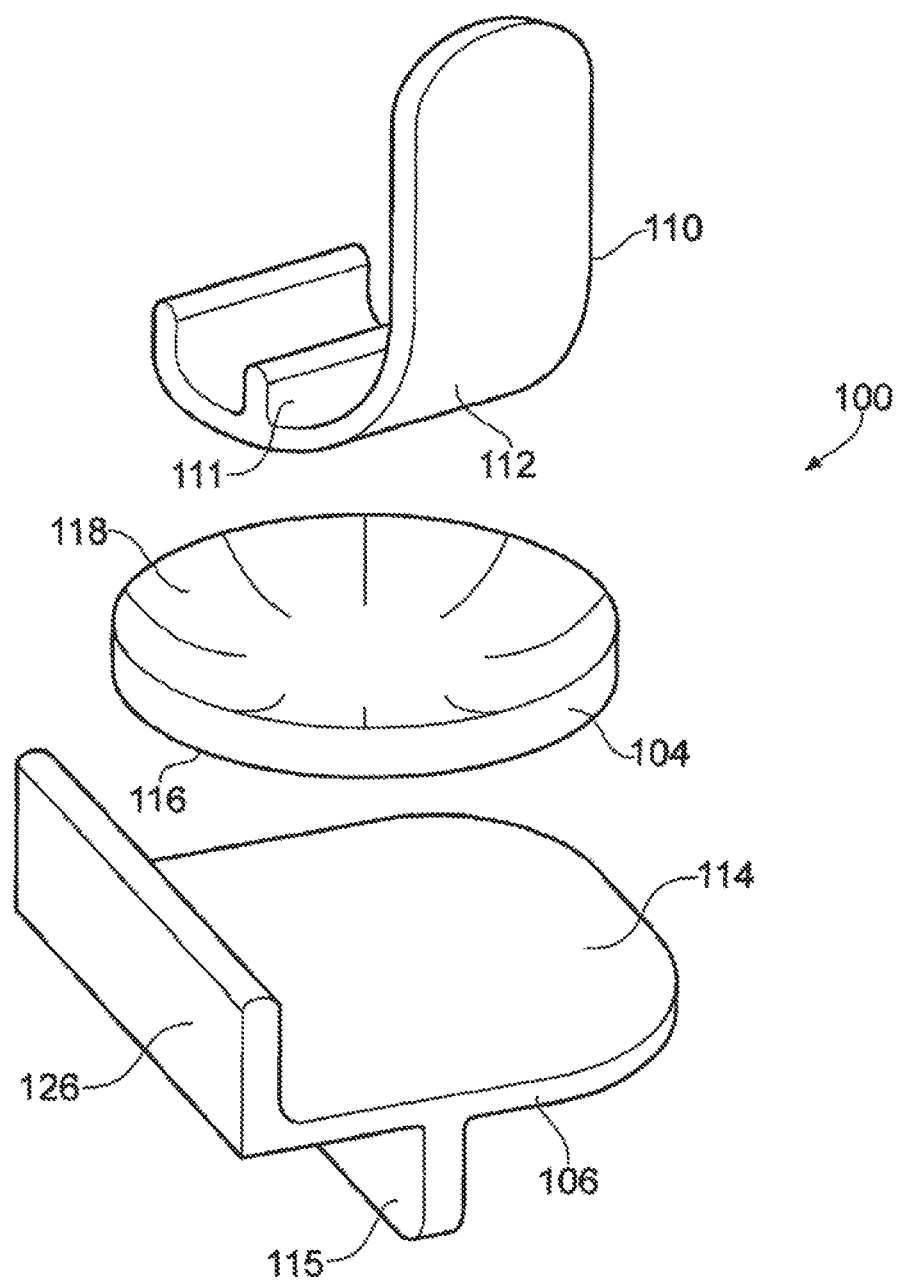
FIG. 1 shows a conventional knee prosthesis comprising a tibial component and a femoral component separated by a bearing component.

FIG. 1 shows a prosthesis 100 suitable for use as a unicompartmental medial artheroplasty of a knee joint.

The prosthesis 100 comprises a bone attachment component configured to support a bearing component 104. In the example shown in FIG. 1, the bone attachment component 102 is a tibial component 106 and the bearing component 104 is a meniscal bearing. The prosthesis comprises a further bone attachment component, for example a femoral component 110 as shown in FIG. 1. The femoral and tibial components 110, 106 may comprise pegs and/or keels 111, 115 to aid fixation to the bone.

The prosthesis comprises a further bone attachment component 102, for example a femoral component 110 as shown in FIG. 1. The femoral and tibial components 110, 106 may comprise pegs and/or keels 111, 115 to aid fixation to the bone.

During the operation to implant the prosthesis 100, the surface of a femoral condyle of a femur bone is prepared for implantation of the femoral component 110 and the surface of a tibial plateau of a tibia bone is prepared for implantation of the tibial component 106.

In the example shown in FIG. 1, the femoral component 110 is configured to be connected to the femoral condyle and comprises an articular bearing surface 112 configured to engage and articulate with the bearing component 104. The tibial component 106 is configured to be connected to the tibial plateau and comprises another articular bearing surface 114, for example a beating support surface, configured to engage and articulate with the bearing component 104.

The prosthesis 100 shown in FIG. 1 is configured to be implanted to the lateral side of the left knee, and so the femoral component 110, the tibial component 106 and the bearing component 104 are configured accordingly. In other examples, the prosthesis 100 may be configured to be implanted to the lateral side of the right knee or the medial side of either the left or right knee. Additionally, the femoral component 110, the tibial component 106 and the bearing component 104 may be supplied in a range of sizes to suit differently sized bones and/or joints.

In the example shown in FIG. 1, the articular surface 114 of the tibial component 106 is planar and is bounded medially by a tibial wall 126 which is formed integrally with the tibial component 106. The corresponding inferior articular surface 116 of the bearing component 104 is planar. The superior articular surface 118 of the bearing component 104 is shaped to receive the articular bearing surface 112 of the femoral component 110. In another example, the articular surface 114 of the tibial component 106 may be domed, for example spherically convex. Accordingly, the inferior articular surface 116 of the bearing component 104 may be spherically concave to match the articular surface 114 of the tibial component 106.

The tibial wall 126 is configured to limit a range of movement of the bearing component 104. For example, the tibial wall 126 may be a vertical wall placed close to or against the sawn vertical surface of the tibial eminence to prevent the beating component from contacting the sawn surface of the tibia bone. Depending upon the configuration of the prosthesis 100, for example a lateral or medial arthroplasty, the tibial wall 126 may be disposed laterally and/or medially of the bearing component 104. In this manner, the tibial wall 126 may mitigate the dislocation, for example the partial medial dislocation, of the bearing component 104 during extremes of varus and/or valgus loading of the prosthesis, and/or at extremes of articulation of the prosthesis 100.

Figure 2:
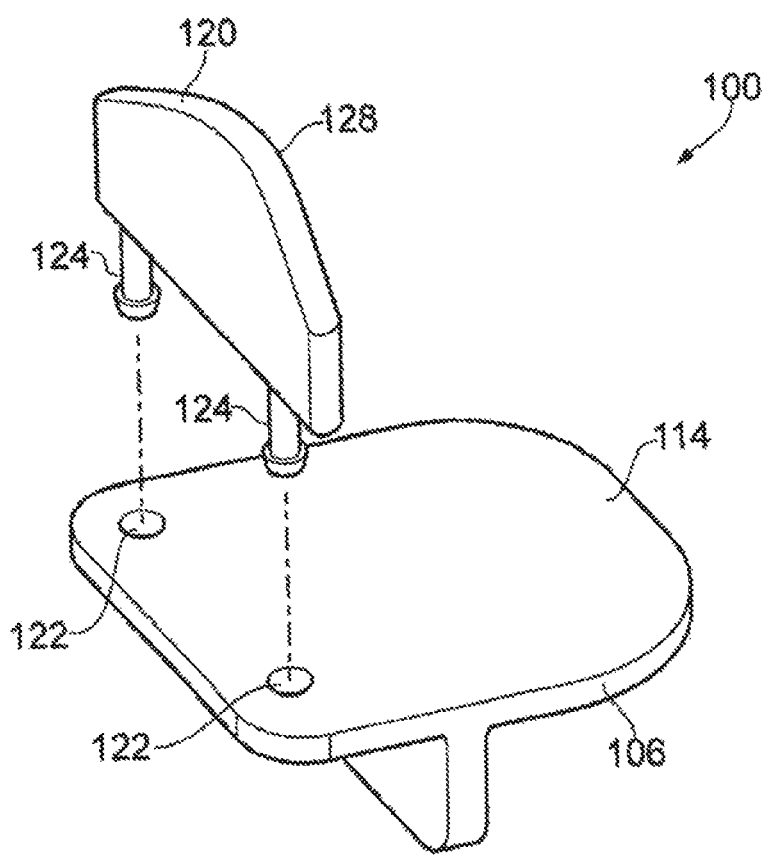
FIG. 2 shows the knee prosthesis comprising a tibial component and a barrier.

FIG. 2 shows a modified prosthesis 100 in which the tibial wall 126 is formed by a barrier 120 which is removably securable to the tibial component 106, and the tibial component 106 may comprise one or more fixation structures 122. The tibial component 106 may be used as part of a mobile or a constrained bearing arthroplasty, and as such, the bearing component 104 may be a mobile bearing component or a constrained bearing component, as discussed below. The barrier 120 may comprise, or be adapted to receive, one or more further fixation structures 124 configured to cooperate with the fixation structures 122 on the tibial component 106. The fixation structures 122, 124 may comprise projections and/or openings. The barrier 120 may be configured to cover the fixation structures on the tibial component 106 such that the bearing component 104 is not able to contact the fixation structures 122, 124.

Figure 3:
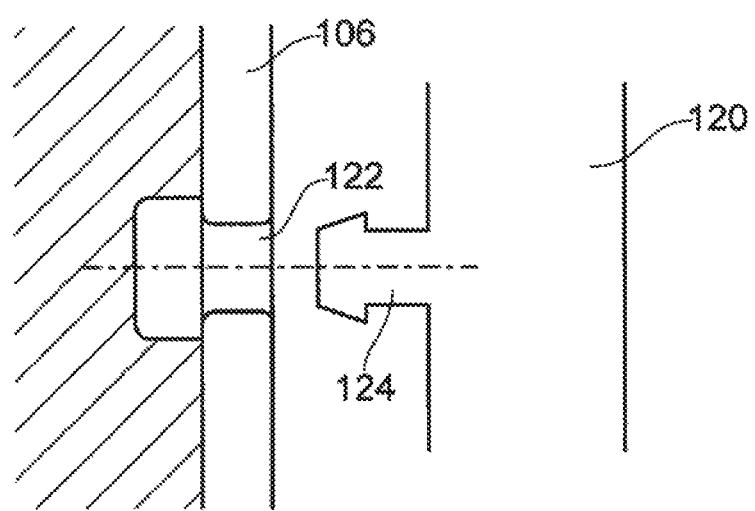
FIG. 3 shows the tibial component and a recess in a tibia bone.

In the example shown in FIG. 2, the tibial component 106 comprises two through-holes disposed on the articular bearing surface 114. The barrier 120 comprises two barbed pegs configured to cooperate with the through-holes on the tibial component 106, although the barrier 120 and the tibial component 106 may comprise any appropriate number of fixation structures 122, 124. It may be appreciated however, the that the openings and the projections may be of any appropriate form that allow the barrier 120 to be removably secured to the tibial component 106. The pegs on the barrier 120 may be a push-fit and/or a snap-fit in the corresponding holes in the tibial component 106. For increased integrity of the fixing, the pegs may protrude into recesses prepared in the bone of the tibial plateau as shown in FIG. 3. Additionally and/or alternatively, one or more further fixation structures, for example wires or pins, may be inserted into the tibial eminence to engage with holes disposed in the pegs. In another example, the tibial component 106 may comprise one or more projections and the barrier 120 may comprise one or more openings, for example blind- and/or through-holes. In another example, the tibial component 106 and the barrier 120 may each comprise a combination of openings and projections.

The barrier 120 may be fabricated from a metallic and/or polymeric material. The barrier 120 may be fabricated from a resilient material and/or may be highly polished in order to mitigate damage to the bearing component 104 upon contact between the bearing component 104 and the barrier 120. The barrier 120 may comprise a metallic structure that is at least partially over-moulded with a polymeric material.

Figure 4:
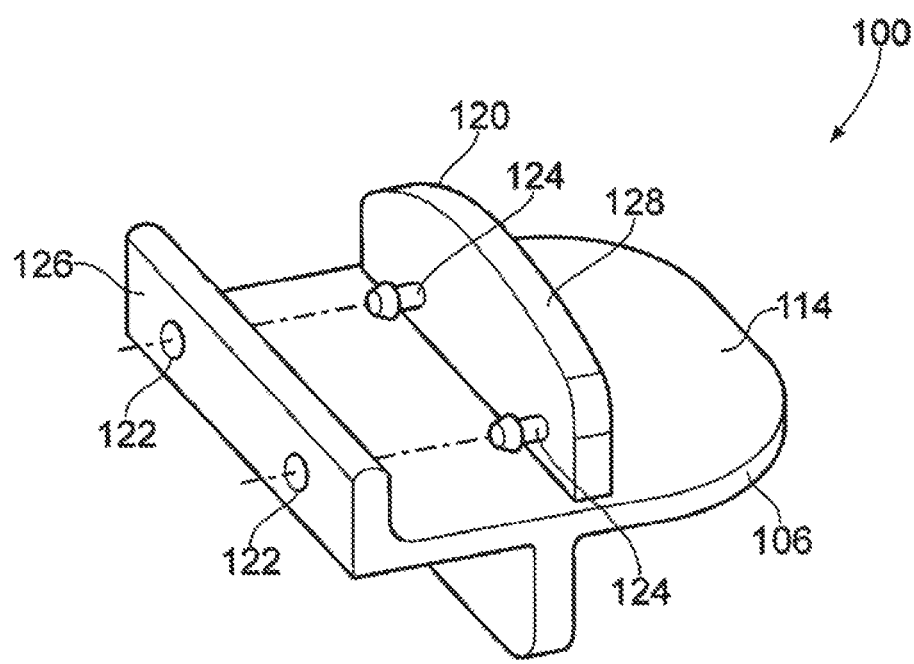
FIG. 4 shows the knee prosthesis comprising the barrier and the tibial component comprising a tibial wall.

FIG. 4 shows a further example of the prosthesis 100, in which the prosthesis 100 is a lateral prosthesis for the left knee. The tibial component 106 comprises an integral tibial wall 126 that extends substantially perpendicular to the articular bearing surface 114 of the tibial component 106. In FIG. 4, the tibial wall 126 is disposed on the medial side of the tibial component 106, but may however be disposed on any other part of the tibial component 106. The surface of the tibial wall 126 that faces the bearing component 104 may comprise at least one planar region and/or at least one curved region. In the example shown, the tibial wall 126 comprises a single planar face extending along the medial side of the prosthesis 100.

In the example shown in FIG. 4, the tibial wall 126 comprises fixation structures 122 and the barrier 120 comprises further fixation structures 124 configured to cooperate with the fixation structures 122 of the tibial wall 126. The barrier 120 may be configured to cover the fixation structures on the tibial wall 126 such that the bearing component 104 is not able to contact the fixation structures 122, 124. In an alternative example, the fixation structures 122 may comprise openings and/or projections that extend in different directions. For example, the fixation structures 122 may comprise a hole or slot in the tibial wall 126, for example near the posererior of the tibial wall 126, and a hole or slot near an anterior edge of the articular bearing surface 114 of the tibial component 106. The barrier 120 may comprise corresponding fixation structures 124, for example pegs and/or pins, that cooperate with the holes in the tibial wall 126 and the articular bearing surface 114 of the tibial component 106.

The barrier 120, as shown in FIG. 4, is configured to extend the height of the tibial wall 126, however, the barrier 120 may be configured to extend the tibial wall 126 in any dimension, for example in its length and/or depth. The superior edge 128 of the barrier 120 may be curved such that the height of the barrier 120 is greater towards the middle of the barrier 120. In this manner, the barrier 120 is configured to help prevent partial medial dislocation of the bearing component 104 during extremes of varus and/or valgus loading of the prosthesis, and/or at extremes of articulation of the prosthesis 100. In an alternative example, the superior edge 128 of the barrier 120 may be profiled in any appropriate manner that helps prevent dislocation of the bearing component.

Figure 5:
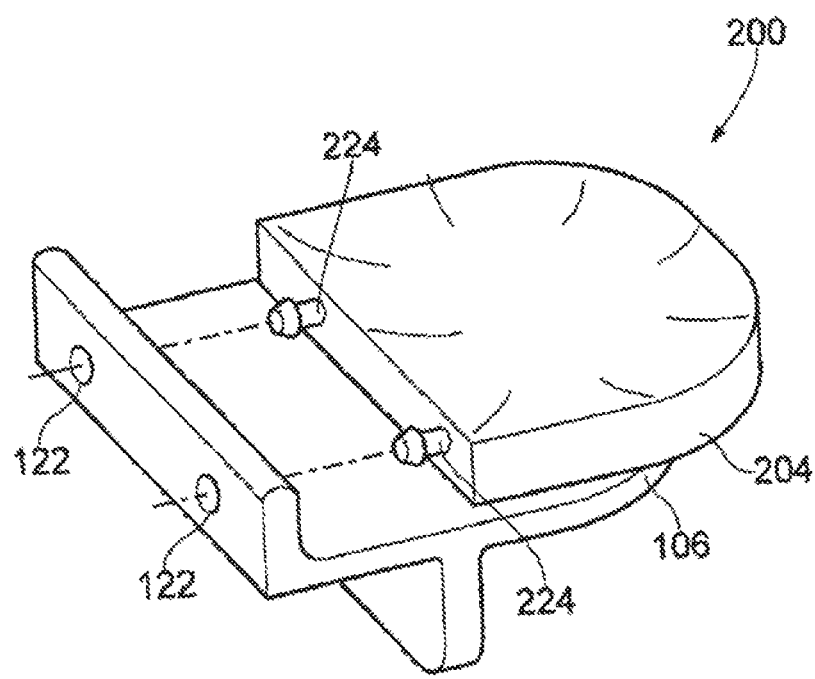
FIG. 5 shows the knee prosthesis comprising a constrained bearing component.

The prosthesis 100 is selectively convertible between the mobile bearing prosthesis 100 of FIG. 4 in which the barrier 120 is secured to the tibial component 106, and the constrained bearing prosthesis 200 of FIG. 5, in which the bearing component 204 is secured to the tibial component 106. This is advantageous as during a primary arthroplasty, the surgeon is able to implant the tibial and femoral components 106, 110 and then selectively attach either the barrier 120 or the bearing component 204 to the tibial component 106 depending upon the damage to and/or the degeneration of the knee joint. If the surgeon decides intra-operatively not to proceed with the mobile bearing prosthesis 100 but wishes to implant a constrained bearing prosthesis 200 instead, the bearing component 204 may be attached to the tibial component 106 using the fixation structures 122 on the tibial component 106 and the fixation structures 224 on the bearing component 204.

Figure 6:
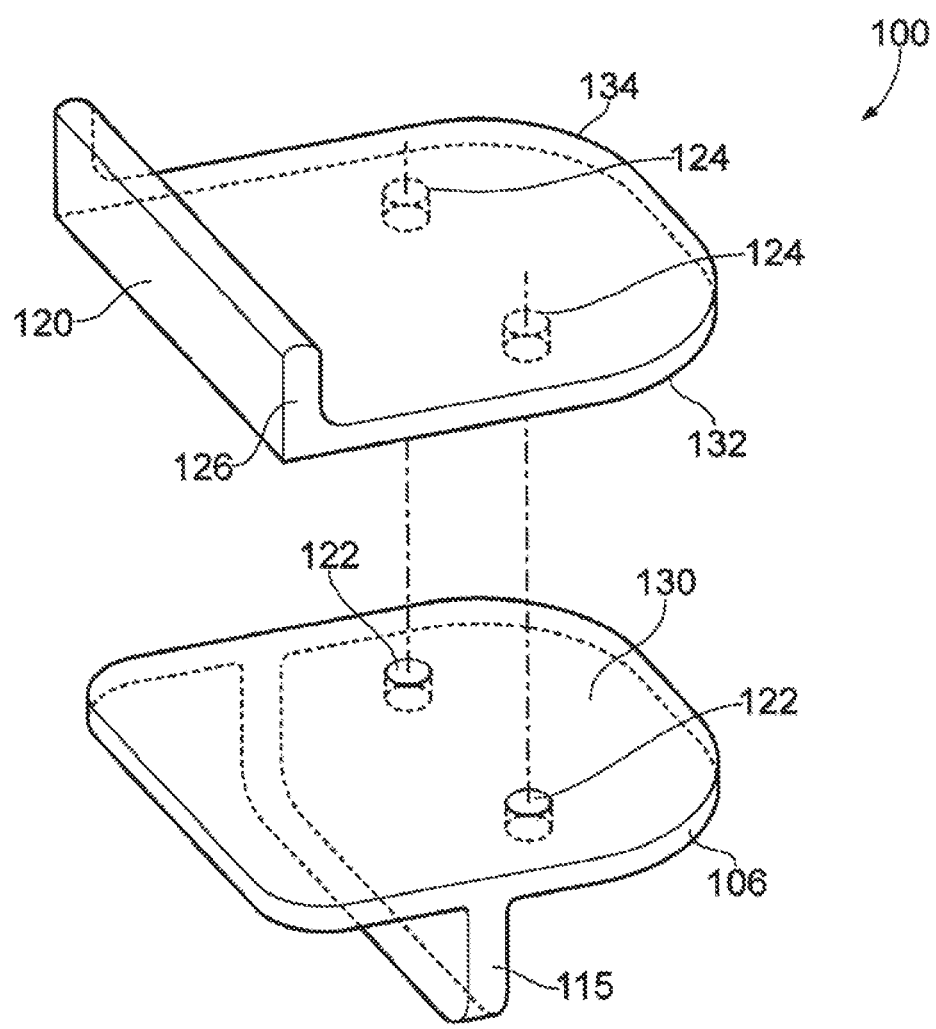
FIG. 6 shows knee prosthesis comprising the barrier having a tibial wall.

FIG. 6 shows a further example of the prosthesis 100, in which the prosthesis 100 is a lateral prosthesis for the left knee. In the example shown in FIG. 6, the tibial component 106 of the prosthesis 100 comprises a surface 130 configured to engage an adjacent surface 132 of the barrier 120. The barrier 120 comprises an articular bearing surface 134 configured to engage and articulate with the bearing component 104 (not shown).

In the example shown in FIG. 6 the barrier 120 comprises the tibial wall 126 which is formed integrally with the barrier 120 and which is disposed on the medial side of the barrier 120. It will be appreciated though that, as with the above-examples, the tibial wall 126 may be disposed on any other part of the barrier 120. The surface of the tibial wall 126 that faces the bearing component 104 may comprise at least one planar region and/or at least one curved region. In the example shown, the tibial wall 126 comprises a single planar face extending along the medial side of the prosthesis 100.

The barrier 120 is configured to cover substantially the surface 130 of the tibial component 106 such that the bearing component 104 is unable to contact the tibial component 106. In another example, the barrier 120 may be configured to cover substantially any portion of the tibial component 106 that is not in contact with the tibia bone.

In the example of FIG. 6, the barrier 120 is located and removably secured to the tibial component 106 by means of fixation structures 124, which are located on surface 132 of the barrier 120, and fixation structures 122, which are located on surface 130 of the tibial component 106. The fixation structures 124 comprise projections, for example pins, that extend from the inferior surface 132, and the fixation structures 122 comprise openings, for example blind holes, that extend into the superior surface 130. As with the previous examples, however, the arrangement of fixation structures 122, 124 may be of any appropriate arrangement that locates and removably secures the barrier 120 to the tibial component 106.

Figure 7:
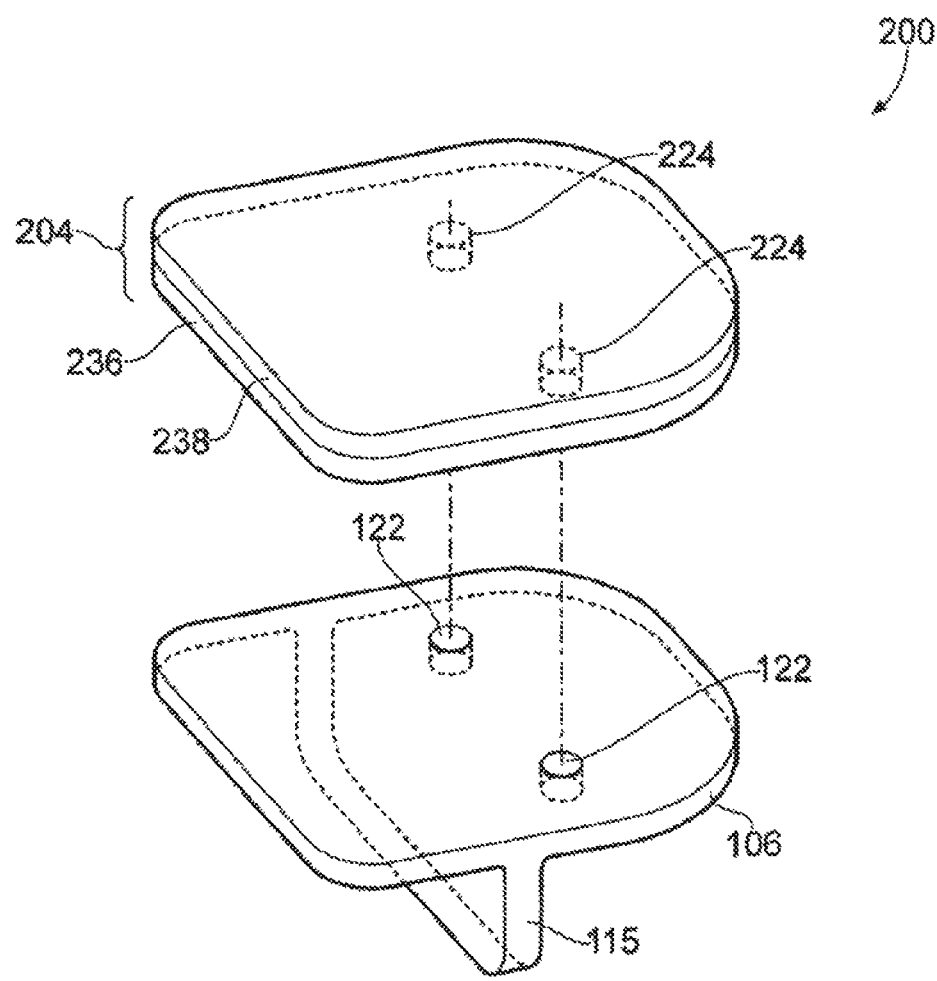
FIG. 7 shows the knee prosthesis comprising another constrained bearing component.

In a similar manner to the examples of FIGS. 4 and 5, the prosthesis 100 is selectively convertible between the mobile bearing prosthesis 100 of FIG. 6, in which the barrier 120 is secured to the tibial component 106, and the constrained bearing prosthesis 200 of FIG. 7, in which the bearing component 204 is secured to the tibial component 106. The bearing component 204 comprises fixation structures 224 configured to engage fixation structures 122 on the tibial component 106. In the example shown in FIG. 7, the bearing component 204 comprises a first portion 236, which is configured to engage the tibial component 106, and a second portion 238, which is configured to engage another bone contacting component, for example the femoral component 110. The first portion 236 may comprise a tray, for example a metallic tray, and the second portion 238 may comprises a polymeric block, for example a polyurethane block, which may, for example, be moulded onto the tray. It is appreciated however, that the bearing component 204 may be unitary or comprise any number of appropriate portions, for example portions with different material properties.

As well as for use in primary arthroplasty, when the constrained bearing component 204 may be attached to the tibial component 106 prior to final implantation, the same or similar constrained bearings components 204 may be used in a revision operation made necessary by the dislocation of the mobile bearing component 104. In such a procedure, following removal of the mobile bearing component 104 and the barrier 120, an introducer may be used to allow the constrained bearing component 204 to be introduced into the joint. The introducer may be configured to align and engage the fixation structures 122, 224 by means of an externally applied force, for example by use of a hammer similar to the tool currently used to hammer the keel of the tibial component of the mobile bearing arthroplasty into a prepared vertical slot in the surface of the tibia.

It may be appreciated that the fixation structures 122, 124, 224 may be configured to at least partially constrain the movement of the barrier 120 and/or the bearing component 204. For example, the bearing component 204 may be partially constrained or substantially constrained, depending upon the configuration of the fixation structures 122, 224. In this manner, the surgeon is able to decide to implant a mobile bearing prosthesis 100, a partially constrained bearing prosthesis or a substantially constrained, e.g. fixed, bearing prosthesis.

Figure 8:
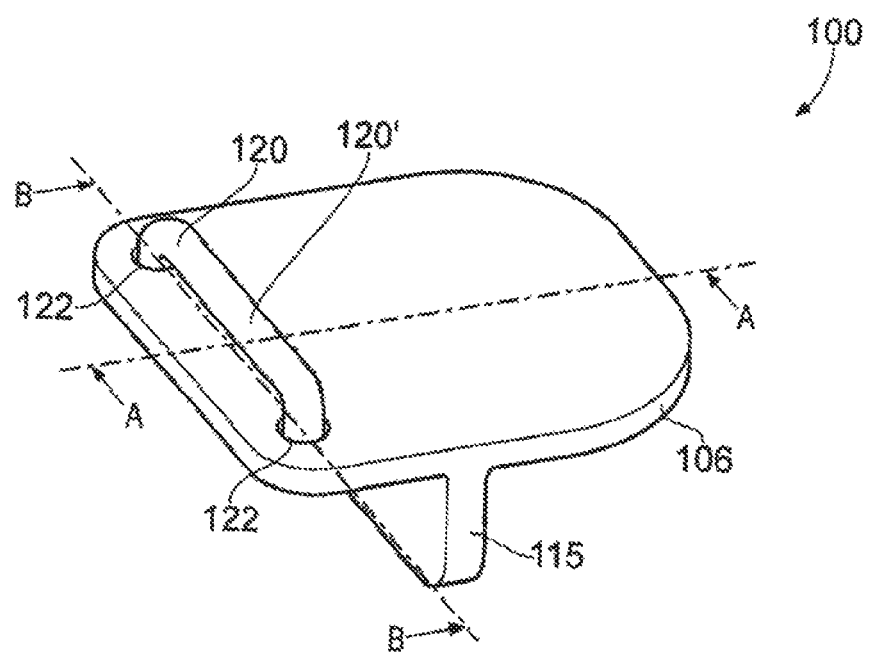
FIG. 8 shows the tibial component and another barrier.
Figure 9:
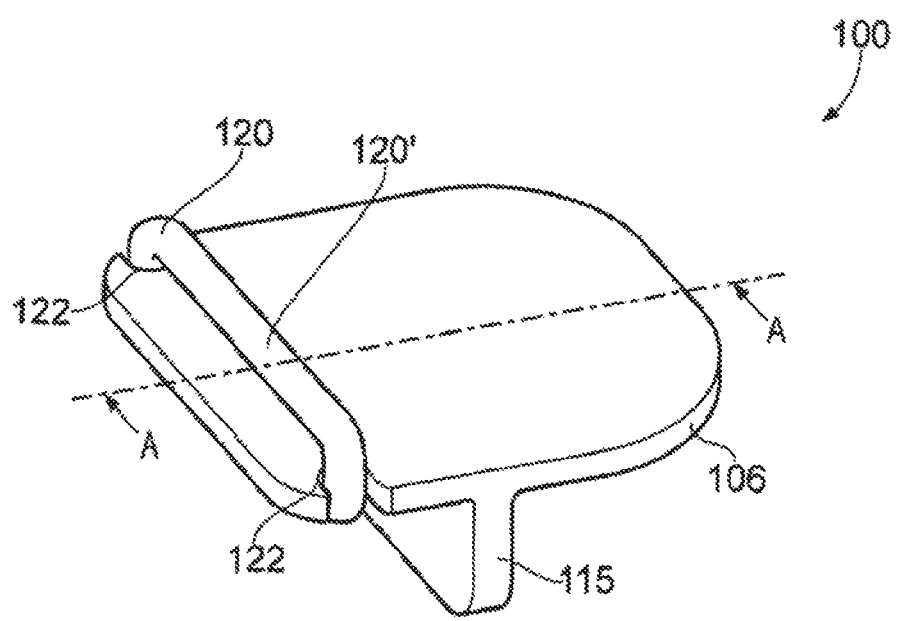
FIG. 9 shows the tibial component and a further barrier.
Figure 10:
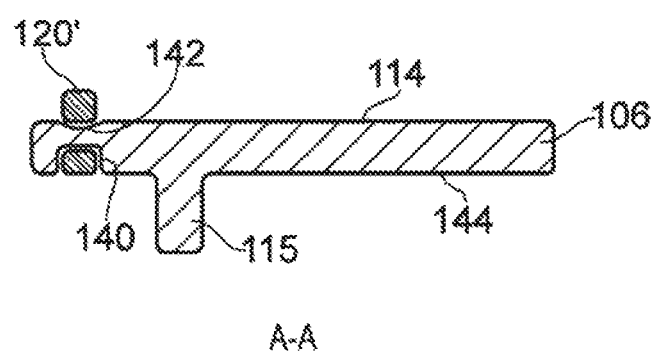
FIG. 10 shows sectional view A-A of FIGS. 8 and 9.
Figure 11:
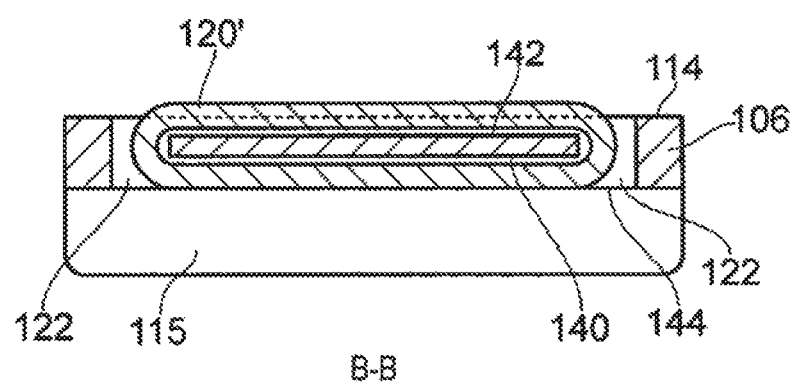
FIG. 11 shows sectional view B-B of FIG. 8.

In another example, as shown in FIGS. 8 to 11, the barrier 120 comprises a band 120', for example a loop or strip of material, that is removably securable to the tibial component 106. The band 120' may for example comprise a flexible polymeric cable or elasticated band. In the example of FIGS. 8, 10 and 11, the fixation structures 122 comprise holes through which the band 120' is threaded. The tibial component 106 comprises grooves 140, 142, as shown in FIGS. 10 and 11, that run between fixation structures 122, such that the band 120' passes through the first of the holes, along the groove 140 in a bone contacting surface 144 of the tibial component 106, through the second of the holes, and along the grove 142 in an opposite surface, which may for example be the articular bearing surface 114. In the example shown in FIGS. 8 to 11, the groove 140 in the bone contacting surface 144 of the tibial component 106 is configured such that the band 120' sits flush with the bone contacting surface 144 and the groove 142 in the articular bearing surface 114 is configured such that the band 120' sits proud of the articular bearing surface 114. In this manner, the band 120' is able to limit the range of movement of the bearing component 104.

In the example shown in FIG. 9, the fixation structures 122 comprise notches in which the band 120' may be seated. It is appreciated however that the tibial component 106 may comprise any combination of fixation structures 122, for example holes, slots and/or notches, that allow the band 120' to be removably secured to the tibial component 106. It is also appreciated that the band 120' may comprise a continuous loop of material that may be stretched over the tibial component 106 such that band 120' is seated in corresponding notches. Alternatively, the band 120' may comprise an open-ended strap, for example a cable tie, that may be passed through and/or wrapped around one or more holes, slots and/or notches.

In a similar manner to the examples of FIG. 4 and FIG. 7, the prosthesis 100 of FIGS. 8 to 11 is selectively convertible between the mobile bearing prosthesis 100, in which the barrier 120, i.e. band 120', is secured to the tibial component 106, and the constrained bearing prosthesis 200 similar to that of FIG. 5 or 7, in which the bearing component 204 is secured to the tibial component 106.

In one example, the band 120' may be attached pre-operatively and conversion of the mobile bearing prosthesis 100 to the constrained bearing prosthesis 200 may be made by cutting band 120', pulling it out from between the tibial component 106 and the bone, and replacing it with bearing component 204.

In another example, the barrier 120, 120' may comprise a resilient clip that is configured to be removably attached to the tibial component 106. The resilient clip may for example be substantially C- or U-shaped, and may be fabricated from a polymer. Alternatively, the resilient clip may comprise a metallic clip that is at least partially over-moulded with a polymeric material. The ends of the resilient clip may comprise one or more fixation structures 124, for example hooks or barbs, configured to retain the resilient clip in fixation structures 122 on the tibial component 106.

The prosthesis 100, 200 comprises a securing element configured to connect the barrier 120 and/or the bearing component 204 to the tibial component 106. The securing element may comprise one or more further fixation structures configured to cooperate with the fixation structures of the tibial component 106, the barrier 120 and/or the bearing component 204. The securing element may be configured to limit the range of movement of the bearing component 204 relative to the tibial component 106. In one embodiment, the securing element may be configured to fix the bearing component 204 relative to the wall, such that the prosthesis 100 becomes a fixed bearing prosthesis. In another embodiment, the securing element is configured to permit a range of movement between the tibial component 106 and the bearing component 204, such that the prosthesis 100 becomes a partially constrained prosthesis. A range of securing elements may be provided so that, upon deciding, the surgeon may select a desired degree of movement of the bearing component 204 relative to the tibial component 106.

Figure 12:
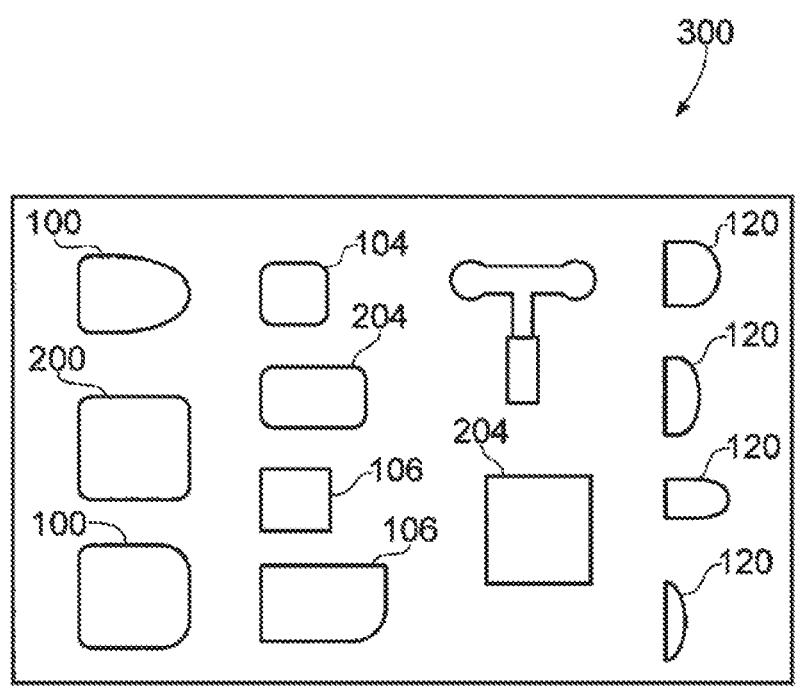
FIG. 12 shows a kit of parts for the knee prosthesis.

Referring to FIG. 12, the prosthesis 100, 200 according to the present invention may be supplied to an end user as a kit of parts. The kit of parts 300 may comprise: at least one of the bearing components 104, 204; at least one bone attachment component 102, for example at least one tibial component 106 and at least one femoral components 110; and at least one barrier 120, for example a short barrier and a taller barrier. The kit of parts 300 may also comprise one or more of the securing elements for use with the prosthesis 100, 200. The kit of parts 300 may comprise one or more tools for use in the implantation and/or removal of any of the components of the prosthesis 100, 200, for example one or more introducers for inserting the bearing component 104, 204 and/or hammers for implanting the bone attachment components.

It will be appreciated by those skilled in the art that although the invention has been described by way of example with reference to one or more examples, it is not limited to the disclosed examples and that alternative examples could be constructed without departing from the scope of the invention as defined by the appended claims.

The invention claimed is:

1. A unicompartmental prosthesis system comprising:
   a first bearing component configured as a mobile bearing component;
   a second bearing component;
   a bone attachment component shaped to be mounted in only a single resected compartment of a tibia, the bone attachment component having a bearing surface for supporting the first bearing component or the second bearing component; and
   a barrier removably securable to a tibial wall of the bone attachment component and configured to limit a range of movement of the first bearing component when utilized with the bone attachment component, wherein the barrier is positioned along a medial or lateral periphery of the bone attachment component and extends proximally from the bearing surface when the barrier is disposed between the first bearing component and the tibial wall, and wherein when the barrier is removed from the tibial wall the second bearing component is configured to be secured to the tibial wall.

2. The system of claim 1, wherein the barrier is securable to the tibial wall with one or more fixation structures and the tibial wall has corresponding one or more fixation structures configured to mate with the one or more fixation structures of the barrier.

3. The system of claim 2, wherein the one or more fixation structures of the barrier comprise projections and the corresponding one or more fixation structures of the tibial wall comprise apertures configured to receive the projections.

4. The system of claim 1, wherein the second bearing component is securable to the tibial wall with one or more fixation structures and the tibial wall has corresponding one or more fixation structures configured to mate with the one or more fixation structures of the second bearing component.

5. The system of claim 4, wherein the one or more fixation structures of the second bearing component comprise projections and the corresponding one or more fixation structures of the tibial wall comprise apertures configured to receive the projections.

6. The system of claim 1, wherein the barrier is configured to extend the tibial wall of the bone attachment component.

7. The system of claim 1, wherein the barrier is configured to prevent partial medial dislocation of the first bearing component.

* * * * *